United States Patent [19]

Reilly

[11] 4,231,736
[45] Nov. 4, 1980

[54] ORTHODONTIC SCREW-TYPE DEVICE AND METHOD OF MAKING SAME

[75] Inventor: Frank Reilly, Freeport, N.Y.

[73] Assignee: Quanta Chemical Ltd., Brooklyn, N.Y.

[21] Appl. No.: 45,304

[22] Filed: Jun. 4, 1979

[51] Int. Cl.³ .............................................. A61C 7/00
[52] U.S. Cl. ........................................................ 433/6
[58] Field of Search ............................................ 433/5

[56] References Cited

U.S. PATENT DOCUMENTS

| | | | |
|---|---|---|---|
| 3,832,778 | 9/1974 | Wallshein | 433/7 |
| 4,107,843 | 8/1978 | Speno et al. | 433/7 |

Primary Examiner—Robert Peshock
Attorney, Agent, or Firm—Frishauf, Holtz, Goodman & Woodward

[57] ABSTRACT

An orthodontic screw-type biassing device comprises: a first member having an internally threaded bore, the threaded bore comprising first and second threaded portions adjacent each other in the axial direction of the bore, the first and second threaded portions having thread roots which lie substantially on a common line, the first threaded portion having threads of given depth and the second threaded portion having threads of a lesser depth. A threaded inner screw-type member is threadably engaged in the internally threaded bore of the member, the threads at an end portion of the inner screw member being deformed so as to freely, threadably pass through the second threaded portion of the threaded bore and to bind and be non-rotatable in the first threaded portion of said threaded bore. The invention is also directed to a method of making such a biassing device.

12 Claims, 4 Drawing Figures

ORTHODONTIC SCREW-TYPE DEVICE AND METHOD OF MAKING SAME

BACKGROUND OF THE INVENTION

This invention relates to an orthodontic screw-type biassing device, and more particularly to such a device including means for preventing the screws from being disengaged from their threaded receptacles.

Screw-type orthodontic devices have been known for many years, one such typical device being illustrated in U.S. Pat. No. 3,832,778 to M. Wallshein. Recently, multi-screw devices, using nested screw arrangements, have been developed, such as those disclosed in U.S. Pat. No. 4,107,843 and in U.S. application Ser. No. 785,587, filed Apr. 7, 1977 by Mr. Wallshein. The entire contents of U.S. Pat. No. 4,107,843 and of U.S. patent application Ser. No. 785,587 are incorporated herein by reference. A problem in the art of designing and fabricating screw-type actuators for orthodontic biassing elements is to prevent the screws from being disengaged from their respective threaded receptables. In the multi-screw arrangement of U.S. Pat. No. 4,107,843, a shoulder-stop arrangement is provided to prevent the larger screw from coming out of its body housing, but there is no means provided for preventing the smaller screw from becoming disengaged from the larger screw. Patent application Ser. No. 785,587 shows various different constructions for preventing disengagement of the screws, both the large screws and the small screws, from their respective threaded receptacles to prevent inadvertent disassembly of the device in the mouth.

The object of this invention is to provide a simplified and easy to manufacture construction for preventing threaded screws from becoming disengaged from their threaded receptacles.

SUMMARY OF THE INVENTION

According to the present invention, an orthodontic screw-type biassing device comprises: a first member having an internally threaded bore, the threaded bore comprising first and second threaded portions adjacent each other in the axial direction of the bore, the first and second threaded portions having thread roots which lie substantially on a common line, the first threaded portion having threads of given depth and the second threaded portion having threads of a lesser depth. A threaded inner screw-type member is threadbly engaged in the internally threaded bore of the first member, the threads at an end portion of the inner screw member being deformed so as to freely, threadably pass through the second threaded portion of the threaded bore and to bind and be non-rotatable in the first threaded portion of said threaded bore.

The invention is also directed to a method of making such a biassing device.

DETAILED DESCRIPTION

Figure 1:
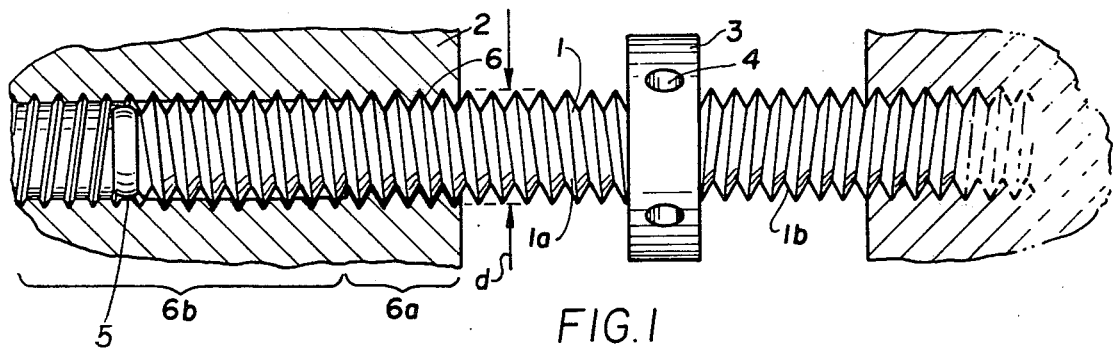
FIG. 1 illustrates a first embodiment of the invention as applied to a single-screw device.

Referring to FIG. 1, which illustrates a single-screw type biassing device, the threaded actuator screw 1 is threadably engaged in a body housing 2, the threaded actuator screw having an engagement spindle portion 3 with holes 4 therein for engagement by an actuator, such as a rod or pin-shaped actuator. The screw 1 is threaded along the complete length thereof, the portions 1a and 1b being oppositely threaded with respect to each other. The end turns of the screw are "turned over" or "hammered down", or otherwise deformed, for example as illustrated at 5. The deformed end turns are normally deformed so that they bind and do not freely turn in the normally threaded portion 6 of the body housing 2. The threaded portion 6 of the body housing 2 is ground down, or otherwise reduced in thread depth, so that the crests of the threads thereof are shortened over the portion 6b of the threaded portion 6. The threads over the portion 6a remain intact. The turned down end threads 5 of the threaded member 1 are deformed such that they pass freely through the area 6b of the threaded portion 6, but bind on the unaltered threaded portion 6a so as to prevent further rotation of the threaded member 1 relative to the body housing 2. This construction results in an easy to manufacture, reliable arrangement to prevent the threaded actuator screw 1 from becoming inadvertently disengaged from the threaded portion 6 of the body housing 2.

Figure 2:
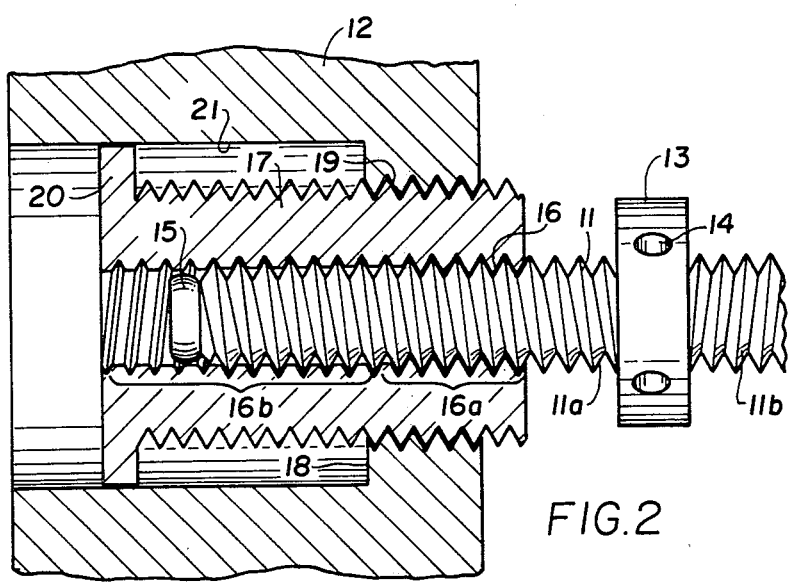
FIG. 2 illustrates a second embodiment of the invention as applied to a nested screw device.

FIG. 2 illustrates a nested screw configuration for a biassing device according to the present invention. The body housing 12 has an unthreaded bore 21 therein which terminates at a shoulder 18 and a threaded portion 19. The outer screw 17 is threaded on its outer periphery so as to mesh with threads 19 of the body housing 12, the outer screw 17 further having a flange or abutment portion 20 which, when the screw 17 is threaded out of the body housing, abuts against shoulder 18 to serve as a stop to prevent disengagement of the screw 17 from the body housing 12. The inner surface of outer screw 17 has threads 16 thereon, substantially the same as threads 6 of FIG. 1. Threads 16 comprise completely threaded portions 16a and threaded portions 16b wherein the crests of the threads have been ground or otherwise reduced in size. The inner screw 11 has a threaded portion 11a and an oppositely threaded portion 11b on opposite sides of the spindle 13. The end turns of the screw 11 are turned down or otherwise deformed, as indicated at 15, so that the turned down end turns 15 may freely pass through the reduced threads 16b, but bind or otherwise interfere with the fully threaded portions 16a of the outer screw 17. Thus, this serves as a stop to prevent complete unthreading of screw 11 from the inner threads 16 of screw 17.

The roots of threads 6a, 6b (and also threads 16a, 16b) lie on a common line (i.e., they have a common major diameter d). The thread depth, i.e., the distance between the root and crest, is less in the portion 6b (and also 16b) than in the portion 6a (and 16a). That is, the threaded portions 6a and 6b have different minor diameters.

Figure 3:
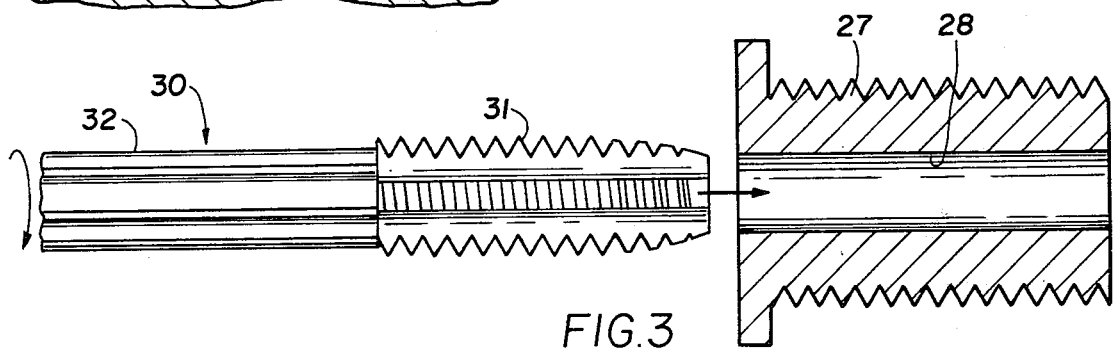
FIG. 3 illustrates a method of fabricating a screw-type device of the present invention.

FIG. 3 illustrates a member 27 which is threaded on the outer surface thereof and which has a bore 28 formed therein. A rotatably driven tool 30 has a forward tapping portion 31 which cuts threads in the inner bore 28 of member 27. The tool 30 has a rear cutting or milling-type portion 32 which cuts the peaks off of the threads which are cut on the inner surface of member 27 by the tapping portion 31. Therefore, in one operation, the completely threaded portions 16a and the reduced crest threaded portion 16b of the member 17 in FIG. 2 is formed. In use, the tool 30 is passed into the bore 28 sufficiently so that the rear cutting portion 32 does not damage the forward threaded portion 16a (FIG. 2). In this manner, the member 27 is formed into the member 17 of FIG. 2.

As an alternative method of FIG. 3, a tool could be provided similar to the tool of FIG. 3, but with a drill bit-type tip at the forwardmost end thereof. In this case, the member 27 need not have the bore 28 pre-formed therein. By using such a composite tool, the bore is first drilled, the tap which is rearward of the drill taps the interior and the cutting surface which is rearward of the tap cuts down the crests of the formed threads.

Figure 4:
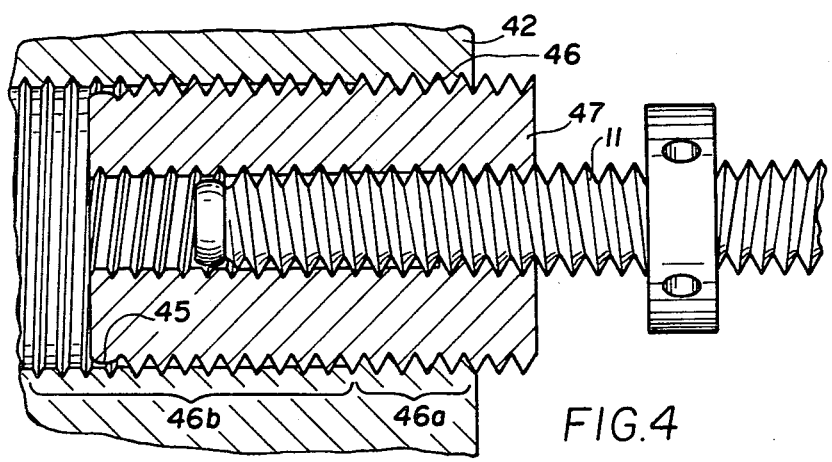
FIG. 4 illustrates a further embodiment of the invention as applied to a nested screw device.

While FIG. 2 illustrates an arrangement wherein the present invention is used to prevent an inner screw 11 from becoming disengaged from an outer screw member 17, the inventive concept may also be applied to prevent the outer screw of a nested screw arrangement from becoming disengaged from the body housing member, for example as illustrated in FIG. 4. As shown in FIG. 4, a body housing 42, which is preferably similar in shape and function to the body housings shown in U.S. Pat. No. 3,832,778 and in U.S. application Ser. No. 785,587, has a threaded bore 46 which comprises fully threaded portions 46a and threaded portions 46b with the crests of the threads removed, such as in threaded sections 6b and 16b in FIGS. 1 and 2. An intermediate threaded member 47 is threadably engaged in the threaded bore 46 with the outer threads thereof being full depth threads which normally fully engage the internally threaded portion 46a of the body member 42. The end turns or threads 45 of the intermediate member 47 are turned down or otherwise deformed as indicated at 45 so that the deformed portion 45 is threadably passable through the threaded portion 46b, but binds in the fully threaded portion 46a, thereby preventing the intermediate member 47 from being fully unthreaded from the body member 42. The embodiment of FIG. 4 also comprises an inner threaded member 11 which may be substantially identical with the inner threaded member 11 of FIG. 2. Intermediate threaded member 47 preferably has internal threads thereon identical with threads 16a, 16b in FIG. 2, the end turn of threaded inner member 11 being turned down, such as at 15 in FIG. 2.

Alternatively, the inner threaded member 11 of FIG. 4 may be threaded in a normally threaded internal bore of intermediate member 47 and other means may be provided for preventing the inner thread 11 from becoming disengaged from the inner threads of intermediate member 47.

It should be clear that the various alternative arrangements of the present invention can be used in any combination, as desired, to prevent the respective screws from becoming inadvertently disengaged from their respective threaded receptacles. In FIG. 4, as in FIGS. 1 and 2, only one side of the device is illustrated. Preferably, the device is used with a body housing, or the like, on respective opposite sides of the spindle 13 so that the device may apply a spreading action in the mouth of a patient as the spindle is turned to rotate the oppositely threaded portions on the respective opposite sides thereof.

In a preferred embodiment of the invention, the thread depth of the threaded portion 6b (and also 16b and 36b) is approximately 50 percent of the depth of the threaded portion 6a (and also 16b and 36b). This ratio, however, is not limiting —other ratios between 30 and 70 percent should also provide satisfactory results. The crests of the threads of the portions 6b, 16b and 36b are preferably substantially flat since the creasts are formed by grinding or otherwise removing material from the originally formed screw threads with a rotary type tool. The threads 6a, 6b (and also 16a, 16b and 36a, 36b) have a substantially common pitch, common thread angle and common major diameter d. The screw-type members 1, 11, 17 and 47 are formed so as to mate with their respective threaded receptacles using conventional dimensional tolerances as our standard in the screw art. While the threads are shown as "V" threads, other threads, such as square threads, trapezoidally formed threads, buttress threads, knuckle threads, etc. could be used on the mating threaded parts. Regardless of the type of thread used, the general criteria discussed hereinabove regarding depth of thread over the different portions 6a, 6b; 16a, 16b; and 36a, 36b applies.

While the invention has been described above with respect to specific embodiments and specific methods of manufacture, it should be clear that various modifications and alterations to the apparatus and method may be made within the spirit and scope of the appended claims.

I claim:

1. An orthodontic screw-type biassing device comprising:
    a first member having an internally threaded bore, said threaded bore comprising first and second threaded portions adjacent each other in the axial direction of said bore, said first and second threaded portions having thread roots which lie substantially on a common line, said first threaded portion having threads of given height and said second threaded portion having threads of a lesser height; and
    an externally threaded screw-type member threadably engaged in said internally threaded bore of said first member, an end portion of said screw-type member being deformed so as to freely pass through said second threaded portion of said threaded bore, said deformed end portion abutting at least one thread of said first threaded portion and binding and being non-rotatable relative said first threaded portion of said threaded bore.

2. The biassing device of claim 1 wherein said second threaded portion extends over a greater length of said internally threaded bore than said first threaded portion.

3. The biassing device of either of claims 1 or 2 wherein said deformed said end portion of said screw-type member comprises a turned down theaded portion.

4. The biassing device of either of claims 1 or 2 wherein the thread height of said second threaded portion is approximately one-half the thread height of said first threaded portion.

5. The biassing device of either of claims 1 or 2 wherein the crests of said second threaded portion are substantially flat.

6. The biassing device of claim 5 wherein the thread height of said second threaded portion is approximately one-half the thread height of said first threaded portion.

7. The biassing device of either claims 1 or 2 wherein the threads of said first and second threaded portions have substantially the same thread angle.

8. The biassing device of claim 7 wherein said threads of said first and second threaded portions have substantially the same pitch.

9. The biassing device of either of claims 1 or 2 wherein said threads of said first and second threaded portions have substantially the same pitch.

10. The biassing device of either of claims 1 or 2 wherein said threaded screw-type member is an intermediate screw member having an internally threaded bore, said internally threaded bore of said intermediate screw member comprising first and second threaded portions adjacent each other in the axial direction thereof, said first and second threaded portions of said bore of said intermediate screw member having thread roots which lie substantially on a common line, said first threaded portion of said bore of said intermediate screw member having threads of given height and said second threaded portion of said bore of said intermediate screw member having threads of a lesser height, and further comprising an inner screw member having external threads thereon and which is threadably engaged in said internally threaded bore of said intermediate screw member, an end portion of said inner screw member deformed so as to freely pass through said second threaded portion of said threaded bore of said intermediate screw member, said deformed end portion of said inner screw member abutting at least one thread of said first threaded portion of said intermediate screw member and binding and being non-rotatable relative to said first threaded portion of said threaded bore of said intermediate screw member.

11. The biassing device of claim 1 wherein said deformed end portion abuts at least a crest of said at least one thread of said first threaded portion.

12. The biassing device of claim 10 wherein said deformed end portion of said inner screw member abuts at least a crest of said at least one thread of said first threaded portion of said intermediate screw member.

* * * * *